(12) United States Patent
Hilaire (10) Patent No.: US 6,428,557 B1
(45) Date of Patent: Aug. 6, 2002

(54) CATHETER SYSTEM FOR RELEASE OF EMBOLIZATION COILS BY HYDRAULIC PRESSURE

(75) Inventor: Pierre Hilaire, Paris (FR)

(73) Assignee: Arthesys, SA, Gennevilliers (FR)

( * ) Notice: Subject to any disclaimer, the term of this patent is extended or adjusted under 35 U.S.C. 154(b) by 0 days.

(21) Appl. No.: 09/406,047

(22) Filed: Sep. 27, 1999

(51) Int. Cl.$^7$ .............................................. A61M 29/00
(52) U.S. Cl. ...................................................... 606/200
(58) Field of Search ................................ 606/200, 195, 606/108

(56) References Cited

U.S. PATENT DOCUMENTS

| | | | |
|---|---|---|---|
| 5,217,484 A | * 6/1993 | Marks | 606/200 |
| 5,261,916 A | * 11/1993 | Engelson | 606/108 |
| 5,350,397 A | * 9/1994 | Palermo et al. | 606/108 |
| 5,417,708 A | * 5/1995 | Hall et al. | 606/200 |
| 5,800,455 A | * 9/1998 | Palermo et al. | 606/200 |
| 5,814,062 A | * 9/1998 | Sepetka et al. | 606/108 |
| 5,895,391 A | * 4/1999 | Farnholtz | 606/200 |

\* cited by examiner

Primary Examiner—Cary E. O'Connor
(74) Attorney, Agent, or Firm—James J. Leary (57) ABSTRACT

Apparatus and methods are described for treating cardiovascular diseases with an embolization coil placement system utilizing an embolization coil and a pusher device. The embolization coil includes a releasable attachment assembly with a deformable ring-shaped member for connecting the embolization coil to a hydraulic pressure actuated coil release assembly on the pusher device. The coil release assembly includes a coil mounting wire with a bulbous distal portion that extends distally from a proximal tubular portion of the pusher device. A small inflatable balloon is mounted on the pusher device surrounding the coil mounting wire and fluidly connected to the proximal tubular portion. The embolization coil delivery system is prepared for use by crimping the deformable ring-shaped member around the deflated balloon member and the mounting wire. The bulbous distal portion of the mounting wire retains the crimped ring-shaped member on the pusher device. A target site in the vascular system is catheterized with a microcatheter. Then, the pusher device with the embolization coil mounted on it is inserted into the microcatheter and advanced to the target site. Once the embolization coil is in position, the inflatable balloon is pressurized with a syringe or inflation device connected to a hub on the proximal tubular portion of the pusher device. As the inflatable balloon member expands, it deforms the ring-shaped member to release the embolization coil from the pusher device. The balloon member is then deflated and the pusher device is withdrawn. In this way, one or more embolization coils may be inserted to occlude the target site by creating a physical barrier to blood flow and encouraging thrombus formation.

28 Claims, 4 Drawing Sheets

CATHETER SYSTEM FOR RELEASE OF EMBOLIZATION COILS BY HYDRAULIC PRESSURE

FIELD OF THE INVENTION

The present invention concerns a medical apparatus for placing embolization coils at selected sites within a patient's cardiovascular system for treatment of cardiovascular diseases and vascular anomalies, such as aneurysms, arteriovenous fistulas and vascular shunts. In particular, the invention concerns a catheter system inducing embolization coils and an embolization coil placement device or "pusher" that uses a coil release assembly that is actuated by hydraulic pressure.

BACKGROUND OF THE INVENTION

One of the current treatments for cardiovascular diseases and vascular anomalies, such as aneurysms, arteriovenous fistulas and vascular shunts, utilizes embolization coils which are introduced into the vascular anomaly to occlude it by creating a physical barrier to blood flow and encouraging thrombus formation. Typically, the embolization coils are placed at the desired location utilizing a microcatheter and an embolization coil placement device, often called a "pusher". First, the site to be treated is catheterized with the microcatheter using flow directed techniques and/or with the aid of a steerable guidewire. Then, after removing the guidewire from the microcatheter, the embolization coil to be deposited is inserted and advanced through the microcatheter with the aid of the pusher. Once the end of the pusher has reached the distal end of the catheter, the embolization coil is pushed completely out of the microcatheter into the intended site. This technique of pushing the embolization coil out of the microcatheter poses a certain number of problems. Positioning the proximal end of the embolization coil cannot be performed with precision and, once the coil has begun to exit the catheter, it is impossible to reposition or to retrieve the embolization coil.

Several techniques have been proposed to permit more precise and controlled placement of embolization coils:

U.S. Pat. Nos. 5,122,136, 5,354,295, 5,540,680, 5,569,245 and 5,743,905 describe different variations of a system of embolization coil placement that uses electrical energy for releasing an embolization coil. The embolization coil is welded to a pusher wire that is used to maneuver the coil into the desired position. The embolization coil remains attached to the pusher wire even when it is pushed beyond the distal end of the microcatheter, which allows the embolization coil to be repositioned or retrieved, if necessary. Once the embolization coil is in the desired position, an electric current is passed through the welded area to electrolytically detach the embolization coil. The electrolytic detachment process is relatively slow, precluding the possibility of instantaneous release of the embolization coil. The electrolytic detachment process may also release deleterious chemical byproducts. In addition, the need for an electrical energy source adds to the cost and complexity of the embolization coil placement system.

U.S. Pat. No. 5,108,407 describes an embolization coil detachment system using light energy delivered through an optical fiber. The embolization coil is bonded to the pusher with a heat sensitive adhesive. When the embolization coil is in the desired position, laser energy is directed through the optical fiber to break the attachment. The laser ablation of the adhesive bond may possibly release undesirable chemical byproducts. In addition, the need for a laser energy source and an optical fiber adds significantly to the cost and complexity of the embolization coil placement system.

Other systems using mechanical embolization coil detachment mechanisms also exist, for example U.S. Pat. Nos. 5,304,195 and 5,261,916. In general, these mechanisms allow retraction of the coil as long as they have not completely exited the catheter, but they release the coil as soon as the pusher exits the distal end of the catheter.

U.S. Pat. Nos. 5,725,534 and 5,234,437 describe mechanical embolization coil detachment mechanisms utilizing a screw thread or a helical coil on the pusher that screws and unscrews from a threaded counterpart on the embolization coil. Proper operation of the coil detachment mechanism depends on precise engagement and disengagement of the threaded parts, which may not always be reliable under difficult clinical conditions.

U.S. Pat. Nos. 5,312,415 and 5,350,397 describe embolization coil placement systems that use a frictional attachment mechanism for controlling the release of the embolization coil. A pusher wire is used to release the embolization coil from the frictional attachment mechanism. The need for a precise interference fit for proper engagement of the frictional attachment mechanism adds significantly to the cost of the embolization coils and the delivery system.

Although these previous devices and systems represent, for the most part, a significant advance in the treatment of vascular disease, there continues to be a great need for improved systems of embolization coil placement that overcome the difficulties and inconveniences attendant with the existing systems.

SUMMARY OF THE INVENTION

In keeping with the foregoing discussion, the present invention provides a system for placement of embolization coils that is simple, reliable and easily achieved using known manufacturing techniques. The system includes an embolization coil and a pusher device for embolization coil placement. The embolization coil is typically constructed of a helically-wound wire coil of a biocompatible metallic alloy wire, or alternatively of a biocompatible polymer or a metal and polymer composite. Additionally, the embolization coil may include fibers or other thrombogenic materials. A releasable attachment assembly extends from the proximal end of the helically-wound wire coil. The releasable attachment assembly is preferably in the form of a deformable ring-shaped member connected to the helically-wound wire coil by an extension member. The ring-shaped member may be a simple annulus or it may have a convoluted or Z-shaped configuration.

The pusher device has a proximal tubular portion connected to a hydraulic pressure actuated coil release assembly. The hydraulic pressure actuated coil release assembly has an embolization coil mounting wire that extends distally from the proximal tubular portion. The mounting wire has a larger diameter distal portion that may be spherical, ellipsoidal, cylindrical or bulbous in shape. A small inflatable balloon member is mounted on the pusher device surrounding the embolization coil mounting wire and fluidly connected to the proximal tubular portion.

The embolization coil delivery system is prepared for use by mounting an embolization coil on the hydraulic pressure actuated coil release assembly by crimping the deformable ring-shaped member around the deflated balloon member and the mounting wire. The enlarged diameter of the distal portion of the mounting wire retains the crimped ring-shaped member on the hydraulic pressure actuated coil release assembly of the pusher device. The target site for the embolization coil is catheterized using a combination of microcatheters, flow directed catheters, guiding catheters and/or steerable guidewires. Then, the distal end of the pusher device with the embolization coil mounted on it is inserted into the microcatheter and advanced to the target site. The embolization coil can be advanced and withdrawn and manipulated as necessary to achieved optimum placement within the target site. Once the embolization coil is satisfactorily positioned, the inflatable balloon member is pressurized using a fluid-filled syringe or inflation device. As the inflatable balloon member expands, it deforms the ring-shaped member to release the embolization coil from the pusher device. The balloon member is then deflated and the pusher device is withdrawn. These steps may be repeated as many times as necessary to achieve satisfactory occlusion of the target site by creating a physical barrier to blood flow and encouraging thrombus formation.

The embolization coils and pusher device of the embolization coil placement system may be provided as components of a complete catheterization kit that may also include a combination of microcatheters, flow directed catheters, guiding catheters, steerable guidewires, a syringe or inflation device and instructions for use according to the methods described herein.

The many advantages of the embolization coil placement system of the present invention include: a completely controllable detachment assembly that does not depend on the position of the embolization coil and pusher assembly relative to the delivery catheter; a simple hydraulically actuated system of embolization coil detachment that is nonelectrical and nonmechanical and that does not require additional equipment, such as an electrical source or laser source; instantaneous detachment of the embolization coils; and no release of secondary products due to material ablation or chemical degradation. These and other advantages will be readily apparent to one of ordinary skill in the art upon reading the following detailed description of the invention taken in conjunction with the accompanying drawings.

DETAILED DESCRIPTION OF THE INVENTION

Figure 1:
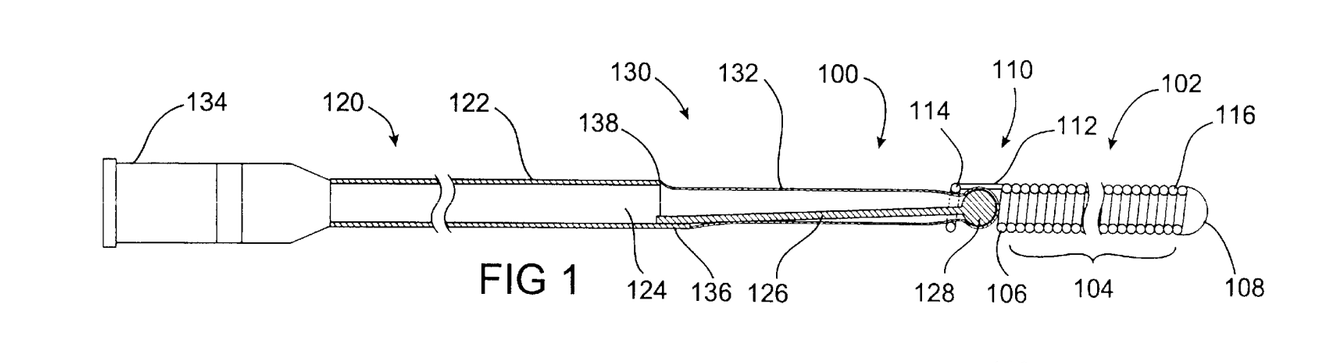
FIG. 1 shows an embolization coil delivery system constructed according to the present invention, including an embolization coil mounted on a pusher device having a hydraulic pressure actuated coil release assembly.

FIG. 1 shows an embolization coil delivery system 100 constructed according to the present invention, including an embolization coil 102 mounted on a pusher device 120 having a hydraulic pressure actuated coil release assembly 130. Preferably, the embolization coil 102 of the embolization coil delivery system 100 is constructed of a helically-wound wire coil 104 having a proximal end 106 and a distal end 108. The helically-wound wire coil 104 will typically have a length of approximately 0.5–60 cm, an outer diameter of approximately 0.2–2 mm and an inner diameter of approximately 0.1–1.7 mm. The nominal outer diameter of the embolization coil 102 is typically given in inches, the most commonly used sizes being 0.010, 0.014, 0.018, 0.035 and 0.038 inches outer diameter. The length of the helically-wound wire coil 104 of the embolization coil 102 is shown truncated in the drawing figures for ease of illustration. Preferably, the helically-wound wire coil 104 is constructed of a biocompatible metallic alloy wire 116 suitable for permanent implantation, such as a stainless steel, cobalt, gold, platinum, tantalum or tungsten alloy. The wire 116 will typically have a diameter of approximately 0.05–0.15 mm. Alternatively, the embolization coil 102 may be constructed of a biocompatible polymer or a metal and polymer composite. If desired the helically-wound wire coil 104 can be formed with a space-filling geometry, such as a helical, spiral or random configuration. In addition, the embolization coil 102 may also include fibers or other thrombogenic materials to hasten occlusion of the target blood vessel after implantation of the embolization coil 102.

Optionally, the distal end 108 of the helically-wound wire coil 104 may be smoothly rounded by welding, brazing or soldering. A releasable attachment assembly 110 extends from the proximal end 106 of the helically-wound wire coil 104. In this exemplary embodiment of the embolization coil 102, the releasable attachment assembly 110 includes a deformable annular ring-shaped member 114 connected to the helically-wound wire coil 104 by an extension member 112. The deformable annular ring-shaped member 114 is preferably made from a malleable metal alloy that is easily deformed or expanded. The annular ring-shaped member 114 is shown in an unexpanded state in FIG. 1 and in an expanded state in FIGS. 2 and 3. The annular ring-shaped member 114 will preferably have an outer diameter similar to that of the helically-wound wire coil 104, typically in the range of approximately 0.2–2 mm. The outer diameter of the annular ring-shaped member 114 in the expanded state will preferably be approximately 110–200 percent of the unexpanded diameter, typically in the range of approximately 0.22–4 mm. In one particularly preferred embodiment, the extension member 112 and the deformable annular ring-shaped member 114 are an extension of the biocompatible metallic alloy wire 116 that makes up the helically-wound wire coil 104. Depending on the alloy chosen for wire 116, the deformable annular ring-shaped member 114 may be heat treated to render it malleable and easily deformed. Alternatively, the deformable annular ring-shaped member 114 and/or the extension member 112 may be made of a separate wire joined to the helically-wound wire coil 104 by soldering, brazing, welding, adhesive or a mechanical attachment.

The pusher device 120 of the embolization coil delivery system 100 has a proximal tubular portion 122 extending proximally from the hydraulic pressure actuated coil release assembly 130. The proximal tubular portion 122 may be constructed of metallic tubing, such as stainless steel hypodermic needle tubing or a nickel/titanium superelastic alloy, or it may be constructed of a rigid polymer, such as polyamide, or it may be an assembly or composite of metal and polymers. The proximal tubular portion 122 may be rigid or semi-rigid, or it may be constructed so that the rigidity varies along the length of the tubular portion 122. The proximal tubular portion 122 will typically have a length of approximately 50–200 cm and an outer diameter of approximately 0.2–2 mm and has an inner lumen 124 with an inside diameter of approximately 0.1–1.7 mm. Preferably, a connector 134, such as a standard female luer lock fitting, is attached to the proximal end of the proximal tubular portion 122 and in fluid connection with the inner lumen 124. Alternatively, a detachable connector, such as a Touhy-Borst connector or a compression fitting may be removably attached to the proximal end of the proximal tubular portion 122.

The hydraulic pressure actuated coil release assembly 130 has an embolization coil mounting wire or rod 126 that extends distally from the proximal tubular portion 122 of the pusher device 120. The rod 126 is preferably made of a metal, such as stainless steel or a nickel/titanium superelastic alloy, and is attached to the proximal tubular portion 122 by soldering, brazing, welding, adhesive or a mechanical attachment. The rod 126 may be attached directly to the interior wall of the proximal tubular portion 122, or the proximal tubular portion 122 may be machined to create a tongue portion 136 extending from its distal end for attachment of the rod 126. On or near the distal end of the rod 126 is an expanded portion 128 having a larger diameter than the proximal portion of the rod 126. The expanded portion 128 may be any convenient shape, such as spherical, ellipsoidal, cylindrical or any bulbous shape, and will preferably have an outer diameter similar to that of the embolization coil 102, typically in the range of approximately 0.2–2 mm. The rod 126 proximal to the expanded portion 128 will typically have a diameter of approximately 0.1–1.5 mm. The rod 126 will typically have a length of approximately 0.1–50 cm. However, in an alternate construction, the rod 126 may run the full length of the pusher device 120 within the proximal tubular portion 122 and attach to the connector 134, particularly if the proximal tubular portion 122 is constructed of a polymer tube. The rod 126 and the expanded portion 128 may be created from a single piece of metal wire by machining, such as by centerless grinding, swaging or stamping. Alternatively, a bead of material may be assembled onto the rod 126 by soldering, brazing, welding, adhesive bonding or mechanical attachment to create an expanded portion 128.

Mounted on the distal end of the pusher device 120, surrounding the rod 126 and the expanded portion 128, is a small inflatable balloon member 132. The inflatable balloon member 132 is shown in a deflated state in FIG. 1 and in an inflated state in FIG. 2. The inflatable balloon member 132 is made of a polymer and can be dip molded from a polymer solution or blow molded from an extruded tube or a molded parison using known methods. Preferably, the inflatable balloon member 132 is made of a relatively low compliance polymer, such as polyamide, polyethylene terephthalate, polyethylene, polyolefin or polyvinyl chloride. Although it is less preferred, an elastic or high compliance inflatable balloon member 132 made of an elastomer, such as polyurethane, silicone or latex, may also be used, particularly if the annular ring-shaped member 114 is made of a soft and highly malleable metal alloy. The inflatable balloon member 132 may be spherical, ellipsoidal or cylindrical in shape and will typically have a length of approximately 2–20 mm and a wall thickness of approximately 0.005–0.050 mm. The inflatable balloon member 132 will preferably have an inflated diameter of approximately 110–200 percent of the diameter of the expanded portion 128 of the rod 126, typically in the range of approximately 0.22–4 mm. The inflatable balloon member 132 has a proximal sleeve 138 that is attached to the distal end of the proximal tubular portion 122 and in fluid connection with the inner lumen 124. The proximal sleeve 138 is adhesively bonded or heat bonded to the proximal tubular portion 122 to create a fluid tight connection. The inflatable balloon member 132 may be formed with a closed distal end 140, as shown, by dip molding on an appropriately shaped mandrel. If the inflatable balloon member 132 is blow molded from an extruded tube, the distal sleeve (not shown) of the blow molded balloon member 132 can be heat sealed or adhesively sealed to create a closed distal end 140 on the balloon member 132. The closed distal end 140 of the balloon member 132 may be adhesively bonded to the expanded portion 128 to stabilize its position on the pusher device 120.

Alternatively, the inflatable balloon member 132 may be formed with a distal sleeve (not shown). In this case, the distal sleeve of the inflatable balloon member 132 may be adhesively bonded to the expanded portion 128 of the rod 126 or onto a distal extension (not shown) of the rod 126 that extends distally from the expanded portion 128.

The embolization coil delivery system 100 is prepared for use by mounting an embolization coil 102 on the hydraulic pressure actuated coil release assembly 130 at the distal end of the pusher device 120. The inflatable balloon member 132 is first deflated by drawing a vacuum on the luer lock connector 134, then the inflatable balloon member 132 is wrapped or folded tightly around the embolization coil mounting rod 126. While vacuum is held on the folded inflatable balloon member 132, the annular ring-shaped member 114 is passed over the expanded portion 128 of the rod 126 while in an expanded state. Then, the annular ring-shaped member 114 is tightly crimped around the folded inflatable balloon member 132 to firmly attach the embolization coil 102 to the pusher device 120. FIG. 1 shows the embolization coil delivery system 100 ready for use with the embolization coil 102 mounted on the pusher device 120. The mounting step can be done in manufacturing so that the embolization coil delivery system 100 is packaged, sterilized and shipped to the end user with a pre-mounted embolization coil 102. Additionally or alternatively, the end user may be furnished with separately packaged sterile embolization coils 102 for mounting on the pusher device 120 immediately prior to use.

Before use, the embolization coil delivery system 100 is prepped by attaching a fluid-filled syringe and a stopcock or other inflation device (not shown) to the luer lock connector 134. If desired, the inflatable balloon member 132 may be vacuum prepped by drawing a vacuum with the syringe to evacuate as much air as possible from the balloon member 132. However, it is important that the inflatable balloon member 132 not be pressurized while prepping the device, as this could lead to premature detachment or loosening of the embolization coil 102. The target site for the embolization coil delivery system 100 is catheterized in the usual way using an appropriate combination of microcatheters, flow directed catheters, guiding catheters and/or steerable guidewires. The target site may be an aneurysm, an arteriovenous fistula or vascular shunt, a feeder artery to a vascular tumor, or any other vascular site or body lumen that is to be embolized or occluded. Then, the distal end of the pusher device 120 with the embolization coil 102 mounted on it is inserted into the microcatheter or guiding catheter and advanced to the target site. Once at the target site, the embolization coil 102 is maneuvered into the desired position with the aid of the pusher device 120. Because the embolization coil 102 is firmly attached to the pusher device 120, it can be advanced and withdrawn and manipulated as necessary to achieved optimum placement of the embolization coil 102. If satisfactory positioning cannot be achieved or if complications arise, the embolization coil 102 can easily be withdrawn into the catheter and removed from the patient.

Figure 2:
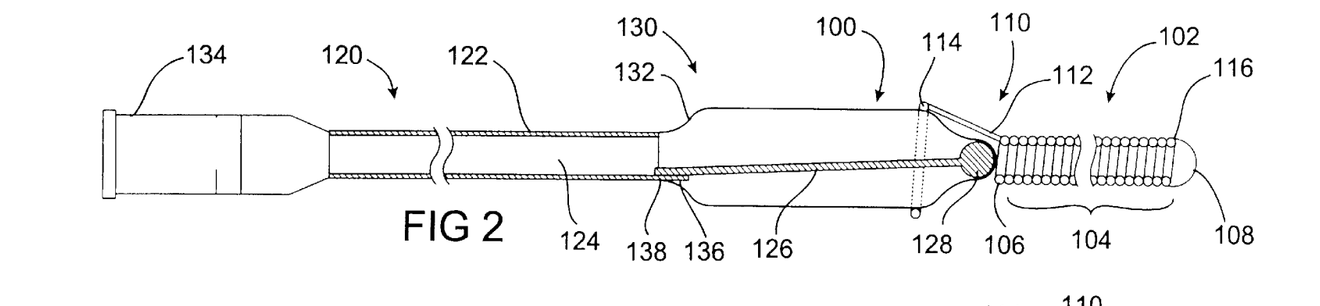
FIG. 2 shows the embolization coil delivery system of FIG. 1, with the balloon of the hydraulic coil release assembly inflated.
Figure 3:
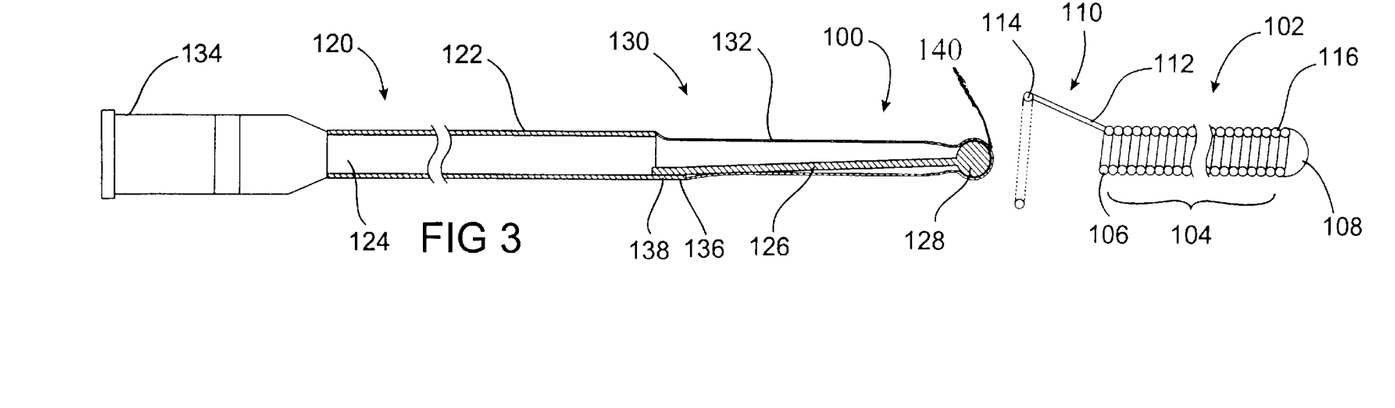
FIG. 3 shows the embolization coil delivery system of FIG. 1, with the balloon of the hydraulic coil release assembly deflated and with the pusher device withdrawn to release the embolization coil.

Once the embolization coil 102 is satisfactorily positioned within the target site, the inflatable balloon member 132 is pressurized using the syringe or inflation device. Hydraulic pressure expands the inflatable balloon member 132, which in turn expands the deformable annular ring-shaped member 114 of the releasable attachment assembly 110, as shown in FIG. 2. To release the embolization coil 102, the balloon member 132 is deflated by drawing a vacuum with the syringe and withdrawing the expanded portion 128 of the rod 126 from the expanded annular ring-shaped member 114, as shown in FIG. 3.

These steps may be repeated as many times as necessary to achieve satisfactory occlusion of the target site by delivering additional embolization coils 102 with the same pusher device 120, or additional embolization coil delivery systems 100 with pre-mounted embolization coils 102 may be used.

The embolization coils 102 and pusher device 120 of the embolization coil placement system 100 may be provided as components of a complete catheterization kit that may also include a combination of microcatheters, flow directed catheters, guiding catheters, steerable guidewires and/or a syringe or inflation device.

Preferably, the embolization coil placement system 100 or a catheterization kit including the system 100 is supplied sterile in a protective package, along with instructions for use according to the methods described herein.

Figure 4:
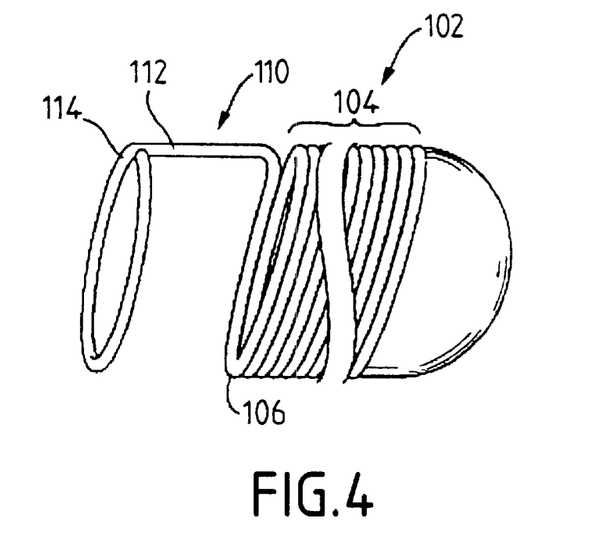
FIG. 4 is a lateral view of a ring-shaped coil attachment assembly on the proximal end of an embolization coil constructed according to the present invention, showing the coil attachment assembly in a closed position.
Figure 5:
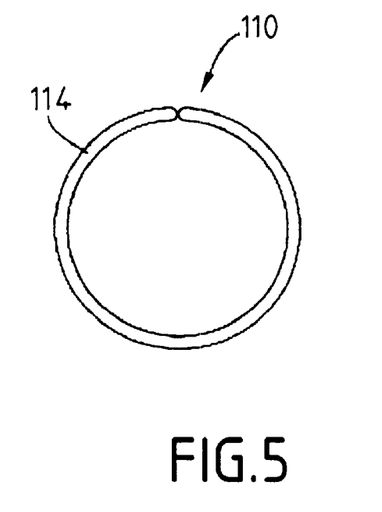
FIG. 5 is a proximal end view of the ring-shaped attachment assembly of FIG. 4 in the closed position.

FIG. 4 is an enlarged lateral view of an embolization coil 102 similar to that shown in FIG. 1 with the releasable attachment assembly 110 shown in the unexpanded or closed position. The pusher device 120 is not shown in this view so that the construction details and operation of the releasable attachment assembly 110 can be better appreciated. The embolization coil 102 has a deformable ring-shaped member 114 that is shaped like an annulus connected to the proximal end 106 of the helically-wound wire coil 104 by an extension member 112. The annular ring-shaped member 114 is in the unexpanded or closed position. FIG. 5 is a proximal end view of the embolization coil 102 of FIG. 4, also shown with the annular ring-shaped member 114 in the closed position. Preferably, the annular ring-shaped member 114 forms a complete circle that is smaller in diameter than the diameter of the expanded portion 128 on the rod 126 of the pusher device 120 when crimped down in the closed position.

Figure 6:
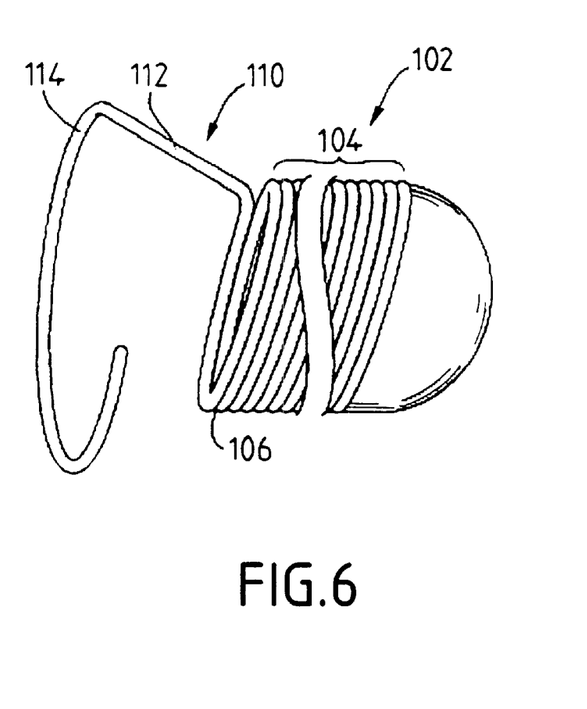
FIG. 6 is a lateral view of the ring-shaped attachment assembly of FIG. 4 with the attachment assembly in an open position.
Figure 7:
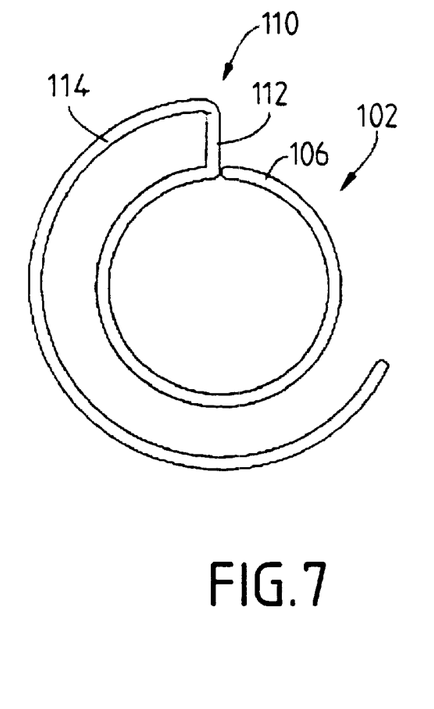
FIG. 7 is a proximal end view of the ring-shaped attachment assembly of FIG. 6 with the attachment assembly in the open position.

FIG. 6 is a lateral view of the embolization coil 102 of FIG. 4 with the attachment assembly 110 in an expanded or open position, similar to that shown in FIGS. 2 and 3. FIG. 7 is a proximal end view of the embolization coil 102 of FIG. 6, also shown with the annular ring-shaped member 114 in the open position. When expanded, the annular ring-shaped member 114 forms an enlarged C-shaped arc that is preferably larger in diameter than the diameter of the expanded portion 128 on the rod 126 of the pusher device 120.

Figure 8:
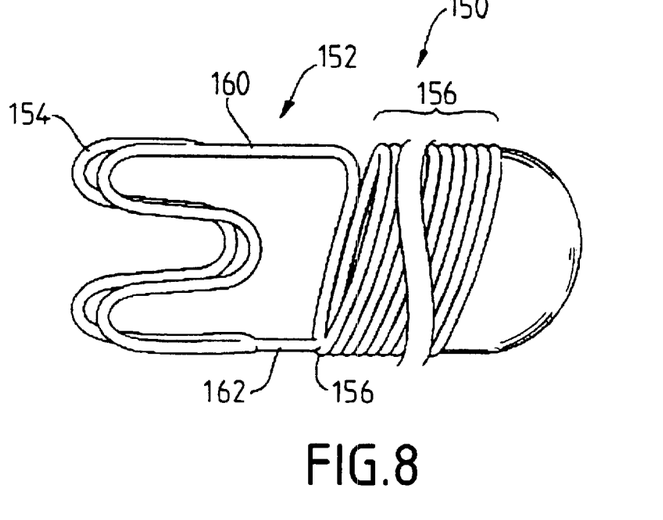
FIG. 8 is a lateral view of a Z-shaped coil attachment assembly on the proximal end of an embolization coil constructed according to the present invention, showing the coil attachment assembly in a closed position.
Figure 9:
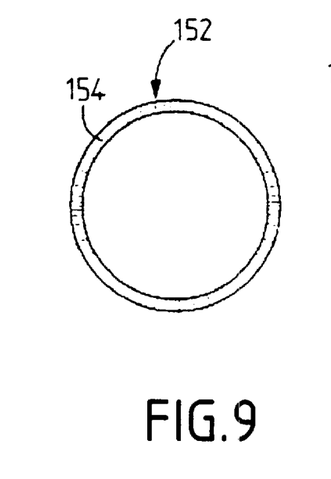
FIG. 9 is a proximal end view of the Z-shaped attachment assembly of FIG. 8 in the closed position.

FIG. 8 is an enlarged lateral view of an alternate construction of an embolization coil 150 according to the present invention. The releasable attachment assembly 152 of the embolization coil 150 is shown in the unexpanded or closed position similar to that shown in FIG. 1. Again, the pusher device 120 is not shown in this view so that the construction details and operation of the releasable attachment assembly 152 can be better appreciated. The embolization coil 150 has a deformable ring member 154 that has a wave-like, convoluted or undulated configuration that can be described as W-shaped or Z-shaped, depending on how it is viewed. This exemplary embodiment of the embolization coil 150 shows only one possible configuration of the Z-shaped deformable ring member 154, many other configurations are possible. The Z-shaped deformable ring member 154 is preferably made from a malleable metal alloy wire that is easily deformed or expanded. The Z-shaped deformable ring member 154 is preferably connected to the proximal end 156 of the helically-wound wire coil 158 by a pair of extension members 160, 162 by welding, brazing, soldering, adhesive or other known attachment techniques. The wire of the Z-shaped deformable ring member 154 may be an extension of the wire that makes up the helically-wound wire coil 158. The Z-shaped deformable ring member 154 is in the unexpanded or dosed position in FIG. 8. FIG. 9 is a proximal end view of the embolization coil 150 of FIG. 8, also shown with the Z-shaped deformable ring member 154 in the closed position. Preferably, the Z-shaped deformable ring member 154 forms a complete circle that is smaller in diameter than the diameter of the expanded portion 128 on the rod 126 of the pusher device 120 when crimped down in the dosed position.

Figure 10:
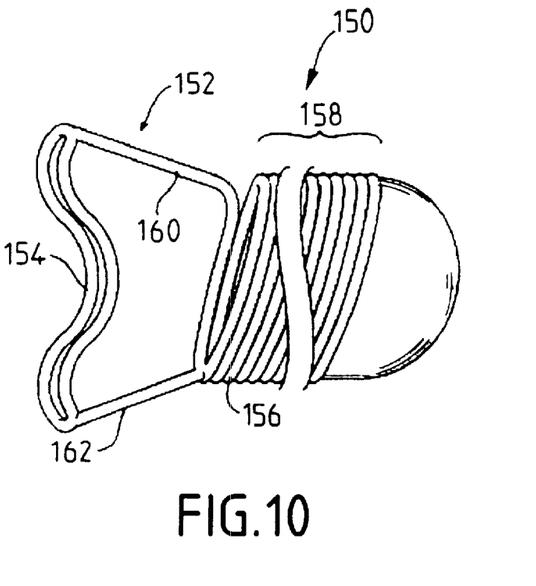
FIG. 10 is a lateral view of the Z-shaped attachment assembly of FIG. 8 with the attachment assembly in an open position.
Figure 11:
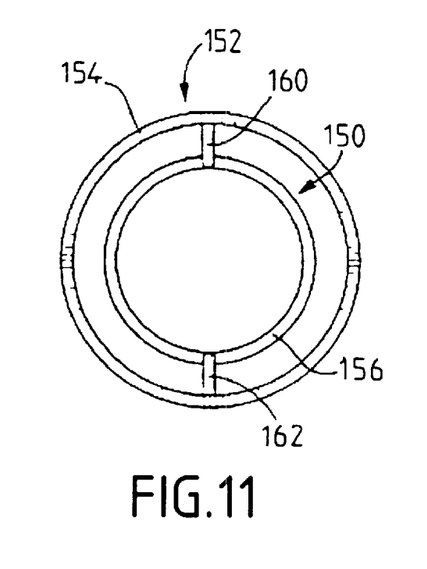
FIG. 11 is a proximal end view of the Z-shaped attachment assembly of FIG. 10 with the attachment assembly in the open position.

FIG. 10 is a lateral view of the embolization coil 150 of FIG. 8 with the attachment assembly 152 in an expanded or open position, similar to that shown in FIGS. 2 and 3. FIG. 11 is a proximal end view of the embolization coil 150 of FIG. 10, also shown with the Z-shaped deformable ring member 154 in the open position. When expanded, the Z-shaped deformable ring member 154 forms an enlarged circle that is preferably larger in diameter than the diameter of the expanded portion 128 on the rod 126 of the pusher device 120.

Figure 12:
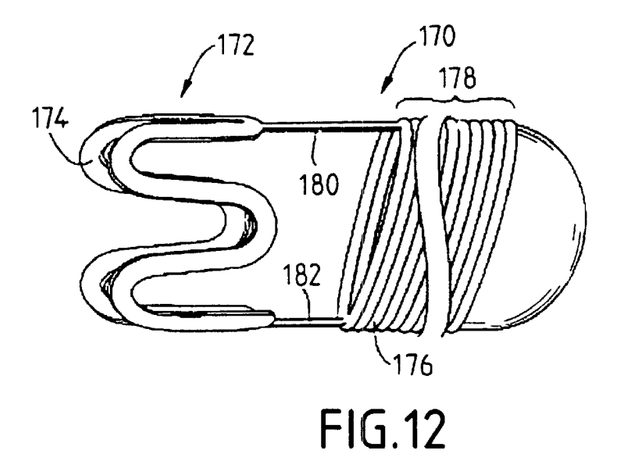
FIG. 12 is a lateral view of an alternate construction of a Z-shaped coil attachment assembly on the proximal end of an embolization coil, showing the coil attachment assembly in a closed position.
Figure 13:
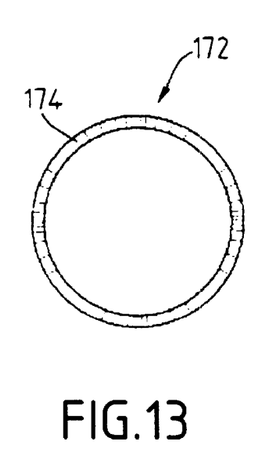
FIG. 13 is a proximal end view of the Z-shaped attachment assembly of FIG. 12 in the closed position.

FIG. 12 is an enlarged lateral view of another alternate construction of an embolization coil 170 according to the present invention. The releasable attachment assembly 172 of the embolization coil 170 is shown in the unexpanded or closed position similar to that shown in FIG. 1. Once again, the pusher device 120 is not shown in this view so that the construction details and operation of the releasable attachment assembly 172 can be better appreciated. The embolization coil 170 has a deformable ring member 174 that has a wave-like, convoluted or undulated configuration that can be described as W-shaped or Z-shaped, depending on how it is viewed. The Z-shaped deformable ring member 174 is preferably made from a thin-walled malleable metal alloy tube that is easily deformed or expanded. The metal alloy tube may be cut out to make the Z-shaped deformable ring member 174 using laser cutting, water jet cutting, abrasive cutting, photo etching or other known metal forming techniques. Alternatively, the Z-shaped deformable ring member 174 may be formed from a polymer or a metal and polymer composite. The Z-shaped deformable ring member 174 is preferably connected to the proximal end 176 of the helically-wound wire coil 178 by a pair of extension members 180, 182 by welding, brazing, soldering, adhesive or other known attachment techniques. This exemplary embodiment of the embolization coil 170 shows only one possible configuration of the Z-shaped deformable ring member 174, many other configurations are possible. The Z-shaped deformable ring member 174 is in the unexpanded or closed position in FIG. 12. FIG. 13 is a proximal end view of the embolization coil 170 of FIG. 12, also shown with the Z-shaped deformable ring member 174 in the closed position. Preferably, the Z-shaped deformable ring member 174 forms a complete circle that is smaller in diameter than the diameter of the expanded portion 128 on the rod 126 of the pusher device 120 when crimped down in the closed position.

Figure 14:
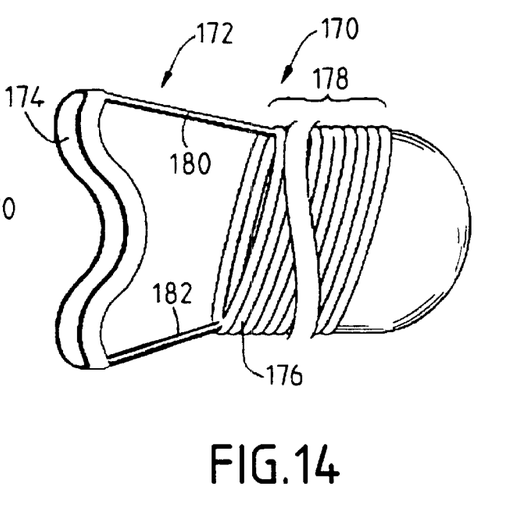
FIG. 14 is a lateral view of the Z-shaped attachment assembly of FIG. 12 with the attachment assembly in an open position.
Figure 15:
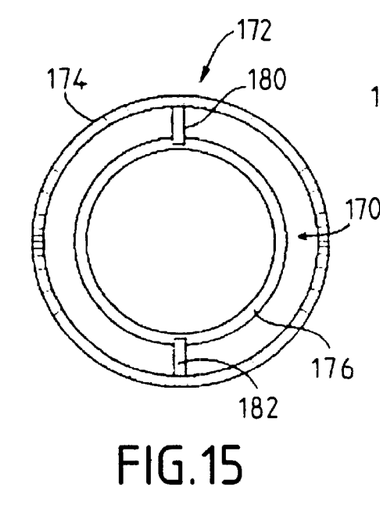
FIG. 15 is a proximal end view of the Z-shaped attachment assembly of FIG. 14 with the attachment assembly in the open position.

FIG. 14 is a lateral view of the embolization coil 170 of FIG. 12 with the attachment assembly 172 in an expanded or open position, similar to that shown in FIGS. 2 and 3. FIG. 15 is a proximal end view of the embolization coil 170 of FIG. 14, also shown with the Z-shaped deformable ring member 174 in the open position. When expanded, the Z-shaped deformable ring member 174 forms an enlarged circle that is preferably larger in diameter than the diameter of the expanded portion 128 on the rod 126 of the pusher device 120.

As may be discerned from the various views of the releasable attachment assemblies in their expanded states, a further advantage of the present invention is that the deformable ring-shaped member may serve as an anchoring member for the embolization coil once deployed. The expanded ring-shaped member, if deployed to a sufficient diameter, may be used to anchor the embolization coil into the target vessel or to interlock multiple embolization coils together to prevent downstream migration of the coils from the intended treatment site.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof.

What is claimed is:

1. Apparatus for treatment of vascular diseases, comprising:

an implantable embolization device; and a delivery device for placement of said embolization device;

wherein said embolization device has a deformable attachment member for attaching said embolization device to said delivery device, and wherein said delivery device includes a pressure actuated release assembly comprising an inflatable balloon for deforming said attachment member, thereby releasing said embolization device from said delivery device, and a mounting wire positioned within said inflatable balloon.

2. The apparatus of claim 1, wherein said attachment member is formed of a malleable metal.

3. The apparatus of claim 1, wherein said delivery device further comprises a tubular proximal portion fluidly connected to said inflatable balloon.

4. The apparatus of claim 3, wherein said mounting wire is affixed to a distal end of said tubular proximal portion.

5. The apparatus of claim 1, wherein said mounting wire further comprises a bulbous portion for retaining said attachment member on said delivery device prior to being released.

6. The apparatus of claim 1, wherein said attachment member comprises a deformable ring-shaped member.

7. The apparatus of claim 6, wherein said deformable ring-shaped member has a convoluted configuration.

8. The apparatus of claim 6, wherein said deformable ring-shaped member has a generally tubular configuration.

9. The apparatus of claim 1, wherein said implantable embolization device comprises a helical wire coil.

10. Apparatus for treatment of vascular diseases, comprising:

an implantable embolization device; and a delivery device for placement of said embolization device;

wherein said embolization device has a deformable attachment member for attaching said embolization device to said delivery device, and wherein said delivery device includes a pressure actuated release assembly for deforming said attachment member, thereby releasing said embolization device from said delivery device;

wherein said delivery device further comprises a tubular proximal portion and a mounting wire, having a bulbous portion, extending distally from said tubular proximal portion, and said pressure actuated release assembly comprises an inflatable balloon surrounding said mounting wire and fluidly connected to said tubular proximal portion;

and wherein said implantable embolization device comprises a helical wire coil and said attachment member comprises a deformable ring-shaped member encircling said inflatable balloon and said mounting wire prior to being released.

11. The apparatus of claim 10, wherein said deformable ring-shaped member has a convoluted configuration.

12. The apparatus of claim 10, wherein said deformable ring-shaped member has a generally tubular configuration.

13. The apparatus of claim 10, wherein said deformable ring-shaped member is an extension of said helical wire coil.

14. The apparatus of claim 10, wherein said tubular proximal portion of said delivery device comprises a metallic tube.

15. The apparatus of claim 10, wherein said delivery device further comprises a connector hub attached to a proximal end of said tubular proximal portion.

16. Apparatus for treatment of vascular diseases, comprising:

a delivery device comprising a tubular proximal portion and a mounting wire, having a bulbous portion, extending distally from said tubular proximal portion, and a pressure actuated release assembly comprising an inflatable balloon surrounding said mounting wire and fluidly connected to said tubular proximal portion; and an implantable embolization device comprising a helical wire coil and an attachment member configured as a deformable ring-shaped member encircling said inflatable balloon and said mounting wire proximal to said bulbous portion.

17. The apparatus of claim 16, wherein said inflatable balloon is inflatable to an inflated diameter at least as large as an outer diameter of said bulbous portion, thereby deforming said attachment member and releasing said embolization device from said delivery device.

18. The apparatus of claim 16, wherein said deformable ring-shaped member has a convoluted configuration.

19. The apparatus of claim 16, wherein said deformable ring-shaped member has a generally tubular configuration.

20. The apparatus of claim 16, wherein said deformable ring-shaped member is an extension of said helical wire coil.

21. The apparatus of claim 16, wherein said tubular proximal portion of said delivery device comprises a metallic-tube.

22. The apparatus of claim 16, wherein said delivery device further comprises a connector hub attached to a proximal end of said tubular proximal portion.

23. A method of therapeutic embolization of a body passage, comprising:

inserting a delivery device, having an inflatable balloon and a mounting wire positioned within said inflatable balloon, with an implantable embolization device mounted thereon, into the body passage;

pressurizing said inflatable balloon on said delivery device to deform an attachment member on said implantable embolization device, thereby releasing said embolization device from said delivery device.

24. The method of claim 23, wherein said implantable embolization device comprises a helical wire embolization coil and wherein the method comprises releasing said embolization col into a patient's blood vessel.

25. The method of claim 23, wherein said delivery device is inserted into a patient's blood vessel through a catheter.

26. The method of claim 23, further comprising withdrawing said delivery device from said body passage after releasing said embolization device from said delivery device.

27. The method of claim 23, further comprising:

prior to inserting said delivery device into the body passage, mounting said implantable embolization device onto said delivery device by crimping said attachment member onto said inflatable balloon and said mounting wire.

28. A method of therapeutic embolization of a body passage, comprising:

inserting a delivery device, having an implantable embolization device mounted thereon, into the body passage;

pressurizing a pressure actuated release assembly on said delivery device to deform an attachment member on said implantable embolization device, thereby releasing said embolization device from said delivery device;

wherein said pressure actuated release assembly comprises an inflatable balloon, and wherein said inflatable balloon is pressurized with a fluid to inflate said inflatable balloon, thereby deforming said attachment member and releasing said embolization device from said delivery device; and wherein said delivery device further comprises a tubular proximal portion fluidly connected to said inflatable balloon and a mounting wire, having a bulbous portion, extending distally from said tubular proximal portion and positioned within said inflatable balloon, said attachment member encircling said inflatable balloon and said mounting wire proximal to said bulbous portion, and wherein said inflatable balloon is inflated to an inflated diameter at least as large as an outer diameter of said bulbous portion, thereby deforming said attachment member and releasing said embolization device from said delivery device.

* * * * *